(12) United States Patent
Domici, Jr.

(10) Patent No.: US 6,471,677 B2
(45) Date of Patent: Oct. 29, 2002

(54) FLUID COLLECTION DEVICE WITH PROTECTIVE SHIELD

(75) Inventor: John K. Domici, Jr., Flemington, NJ (US)

(73) Assignee: GEM Plastics, Inc., Hillsborough, NJ (US)

(*) Notice: Subject to any disclaimer, the term of this patent is extended or adjusted under 35 U.S.C. 154(b) by 0 days.

(21) Appl. No.: 09/824,140

(22) Filed: Apr. 3, 2001

(65) Prior Publication Data

US 2001/0037089 A1 Nov. 1, 2001

Related U.S. Application Data

(60) Provisional application No. 60/194,878, filed on Apr. 6, 2000.

(51) Int. Cl.[7] .................................................. A61M 5/32
(52) U.S. Cl. ........................ 604/198; 604/110; 604/187; 604/263
(58) Field of Search .............................. 604/110, 187, 604/192, 195, 197, 198, 263

(56) References Cited

U.S. PATENT DOCUMENTS

| | | |
|---|---|---|
| 4,723,943 A | 2/1988 | Spencer |
| 4,801,295 A | 1/1989 | Spencer |
| 4,840,185 A | 6/1989 | Hernandez |
| 4,915,702 A | 4/1990 | Haber |
| 4,994,045 A | 2/1991 | Ranford |
| RE33,585 E | 5/1991 | Haber et al. |
| 5,019,051 A | 5/1991 | Hake |
| 5,057,079 A | 10/1991 | Tiemann et al. |
| 5,067,490 A | 11/1991 | Haber |
| 5,137,521 A | 8/1992 | Wilkins |
| 5,219,333 A | 6/1993 | Sagstetter et al. |
| 5,279,584 A | 1/1994 | Dillard, III et al. |
| 5,312,370 A | 5/1994 | Talonn et al. |
| 5,328,473 A | 7/1994 | Fayngold et al. |
| 5,356,392 A | 10/1994 | Firth et al. |
| 5,385,555 A | 1/1995 | Hausser |
| 5,415,645 A | 5/1995 | Friend et al. |
| 5,437,639 A | 8/1995 | Malenchek |
| 5,573,513 A | 11/1996 | Wozencroft |
| 5,658,254 A | 8/1997 | Reichenbach et al. |
| 5,980,494 A | 11/1999 | Malenchek et al. |
| 6,090,077 A | 7/2000 | Shaw |

Primary Examiner—Steven J. Ganey

(57) ABSTRACT

A fluid collection device includes a receptacle for holding a fluid collecting vial and a shield that telescopically receives a portion of the receptacle. The receptacle and shield have closed distal ends with aligned apertures for receiving a vacuum needle. The receptacle is axially displaced within the shield between two releasable locking positions. The first releasable locking position is a "needle exposure" position, wherein the needle is exposed outside of the shield and is ready for use. The second releasable locking position is a "needle storage" position, wherein the needle is completely withdrawn into the shield for protective storage during nonuse. The receptacle has at least one locking tab and at least one engaging tab, and the shield has at least one slot and at least one barrier for receiving and engaging the locking tab and engaging tab, respectively. When in the "needle storage" position, the engaging tab is received within the slot and an edge of the locking tab abuts the barrier to prevent the receptacle from moving axially within the shield beyond a selected distance between the receptacle proximal end and the shield proximal end. The locking tab may further be depressed radially toward the exterior surface of the receptacle to disengage the locking tab from the barrier and release the device from the "needle storage" position.

16 Claims, 2 Drawing Sheets

FLUID COLLECTION DEVICE WITH PROTECTIVE SHIELD

CROSS-REFERENCE TO RELATED APPLICATIONS

This application claims priority from U.S. Provisional Patent Application Serial No. 60/194,878 entitled "Syringe Blood Collector", filed Apr. 6, 2000. The disclosure of this provisional application is incorporated herein by reference in its entirety.

BACKGROUND OF THE INVENTION

1. Field of the Invention

This invention relates to a novel fluid collection device, more particularly, to a fluid collection device having a shield that covers a vacuum needle and protects the user of the device when the needle is not in use.

2. Discussion of the Related Art

A variety of different fluid collection devices, particularly blood collection devices, are used in healthcare facilities such as hospitals and clinics. Each device typically utilizes a vacuum needle protruding from a receptacle for drawing fluid from a source, such as a patient's body, into a vial disposed within the receptacle. A primary concern associated with these devices is protecting the user and others from an accidental strike by the protruding needle when the device is not being used.

To alleviate such concern, many fluid collection devices provide a shield that surrounds the needle when the device is not in use. The shield is further designed in many of these devices to telescopically receive the receptacle to which the needle is attached. For example, U.S. Pat. No. 5,328,473 (Fayngold et al.) discloses a disposable needle holder assembly including an outer sleeve that telescopically receives a needle holder with a needle assembly attached thereto. The needle assembly is attached at the distal end of the needle holder and extends from the distal end of the sleeve during use of the device. The needle holder includes a pair of ramps on its outer surface near its distal end with a groove positioned therebetween. The sleeve includes a segmented annular projection on its interior surface near its proximal end for receiving and holding the ramps on the needle holder. After using the needle holder assembly, the needle is retracted and permanently locked within the sleeve by telescopically moving the needle holder distal end toward the sleeve proximal end until the segmented annular projection on the sleeve locks within the groove located between the ramps on the needle holder. The Fayngold et al. device is limited in that the needle holder assembly is rendered inoperable after shielding the needle within the sleeve, because the needle holder becomes permanently locked within the sleeve upon engagement of the sleeve segmented annular projection with the groove located between the needle holder ramps.

In U.S. Pat. Reissue No. 33,585 (Haber et al.), a shielded safety syringe is disclosed including a syringe cylinder telescopically received within an outer sleeve. A needle is attached to the cylinder distal end and protrudes from the sleeve distal end when the cylinder is completely received within the sleeve. The safety syringe further includes locking members attached to and extending from the outer surface of the sleeve. The locking members are connected to the sleeve via a living hinge assembly at the sleeve proximal end. Each locking member includes a leg that extends into the interior of the sleeve so as to releasably engage with two sets of grooves defined along the outer periphery of the cylinder at its proximal and distal ends. During operation, the needle may protrude from the sleeve distal end while the cylinder is locked within the sleeve by engagement of the legs of the locking members with the proximal groove on the cylinder. After using the syringe, the needle may be retracted within the sleeve upon pivoting the locking members such that the locking member legs disengage with the cylinder proximal groove. The cylinder and needle may further be releasably locked within the sleeve by drawing the cylinder distal end toward the sleeve proximal end until the locking member legs engage with the cylinder distal groove. Although the safety syringe of Haber et al. provides a releasable locking feature allowing the syringe to be repeatedly shielded, the living hinge assembly and corresponding locking members on the sleeve render the safety syringe difficult to manufacture and not easy for mass production. Additional raw material is also required to manufacture the sleeve of Haber et al., in comparison to typical syringe sleeves, due to the locking members that are formed and extend from the sleeve.

In U.S. Pat. No. 5,437,639 (Malenchek), a needle protective sheath device is disclosed including an inner cylindrical member having a pair of opposing axially extending tapered slots extending toward its proximal end and a needle secured to its distal end. The inner member is telescopically received within an outer cylindrical member and has temporary locking projections extending from its sides near its proximal end that engage with locking holes at the proximal end of the outer member. During engagement of the locking projections within the locking holes, the needle extends through the distal end of the outer member. Squeezing the member sides of the inner member proximal end together results in the temporary locking projections disengaging from the locking holes to allow the inner member distal end to be drawn towards the outer member proximal end thus retracting the needle within the outer member. Other projections and locking ramps are on the inner member at its distal end for engaging the locking holes on the outer member. Guide channels in the interior wall of the outer member engage the inner member distal projections and ramps to guide those elements as the inner member and needle are axially displaced with respect to the outer member. The sheath device of Malenchek, while providing a temporary locking feature when the needle extends from the outer member, fails to provide a temporary locking feature when the needle is retracted and the inner member distal projections engage the outer member locking holes. Additionally, the sheath device of Malenchek is expensive to manufacture and requires a substantial deformation of the inner member distal end to disengage the locking projections from the locking holes prior to retracting the needle into the outer member.

Accordingly, there exists a need to provide a fluid collection device with a protective shield that is relatively inexpensive to manufacture, that is safe and easy to use and that provides an easy releasable locking arrangement for both a needle exposure or "use" mode and a needle retraction or "storage" mode.

SUMMARY OF THE INVENTION

An object of the present invention is to provide a fluid collection device with a protective shield that provides a releasable locking arrangement in both a needle "use" mode and a needle "storage" mode. Another object of the present invention is to provide a fluid collection device with a protective shield that is easy to manufacture on a mass production scale.

A further object of the present invention is to provide a fluid collection device with a protective shield that is easy and safe to use, particularly during locking and unlocking of the device when the needle is being moved between operable and inoperable positions.

The aforesaid objects are achieved individually and/or in combination and it is not intended that the present invention be construed as requiring two or more of the objects to be combined unless expressly required by the claims attached hereto.

In accordance with the present invention, a fluid collection device includes a receptacle telescopically received within the cavity of a shield. The shield and receptacle both have open proximal ends and substantially closed distal ends. A vacuum needle is secured to the receptacle distal end and extends from an aperture at the shield distal end when the receptacle is displaced toward the shield distal end.

The receptacle includes at least one engaging tab and at least one locking tab protruding from an exterior surface of the receptacle. The engaging tab is formed by a ramp having an inclined surface increasing in distance radially from the receptacle exterior surface and extending in an axial direction to terminate at an engaging edge facing the receptacle proximal end. The locking tab is located between the engaging tab and the receptacle proximal end and is formed by a ramp having an inclined surface increasing in distance radially from the receptacle exterior surface in an axial direction to terminate at a locking edge facing the receptacle distal end. The shield includes at least one slot defined along a shield interior surface within the shield cavity and dimensioned to engage and hold the engaging tab. The shield further includes at least one barrier formed at the shield interior surface and located a selected distance from the shield slot in a direction toward the shield proximal end.

The receptacle is axially movable within the shield cavity, and the engaging tab and the locking tab are spaced a selected distance from each other such that the locking edge of the locking tab abuts the barrier of the shield when the engaging tab engages the slot to thereby limit or prevent axial movement between the receptacle and the shield. The prevention or limitation of such movement provides for secured retraction of the needle within the shield when not in use. Additionally, the locking tab may be radially deformed toward the exterior surface of the receptacle to allow release of the locking edge from abutment with the barrier of the shield, thereby freeing the receptacle from its locked position and facilitating continued axial movement of the receptacle with respect to the shield.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

DESCRIPTION OF THE PREFERRED EMBODIMENTS

Figure 1:
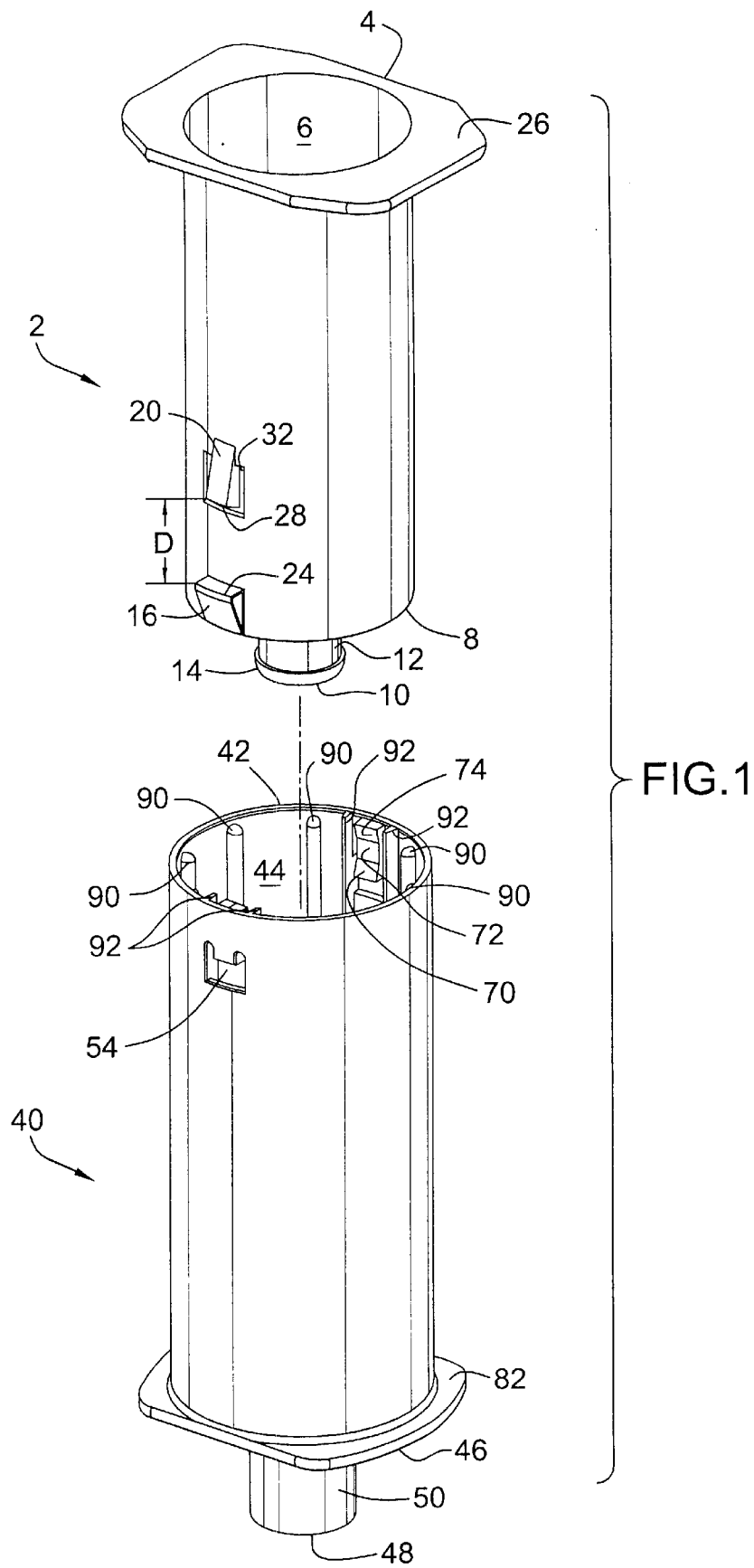
FIG. 1 is an exploded view in perspective of a fluid collection device according to the invention.
Figure 2:
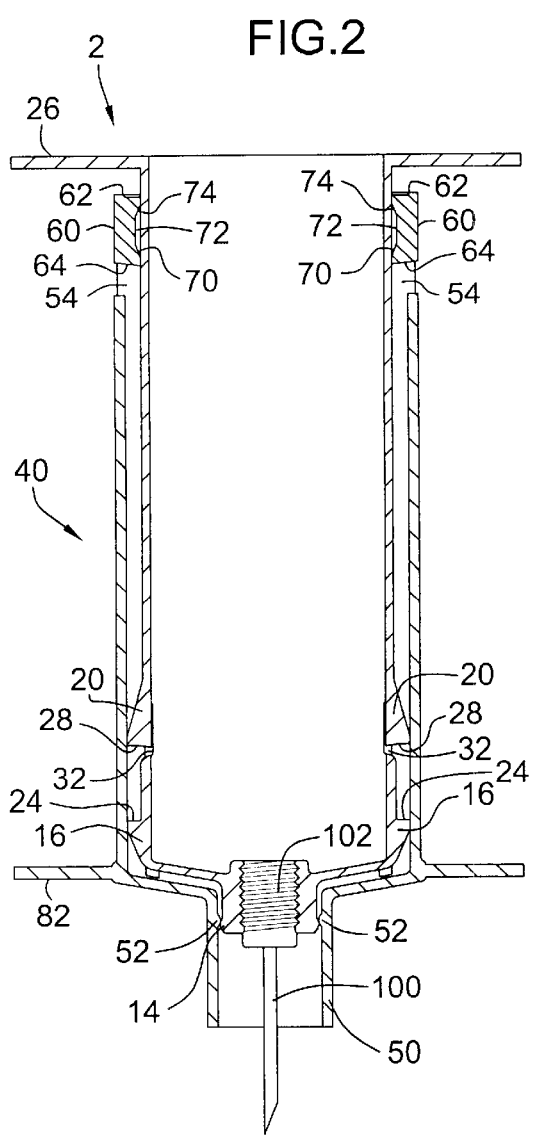
FIG. 2 is a view in longitudinal section of the fluid collection device of the invention with the receptacle in a locked position with respect to the shield and the needle extending from the shield.
Figure 3:
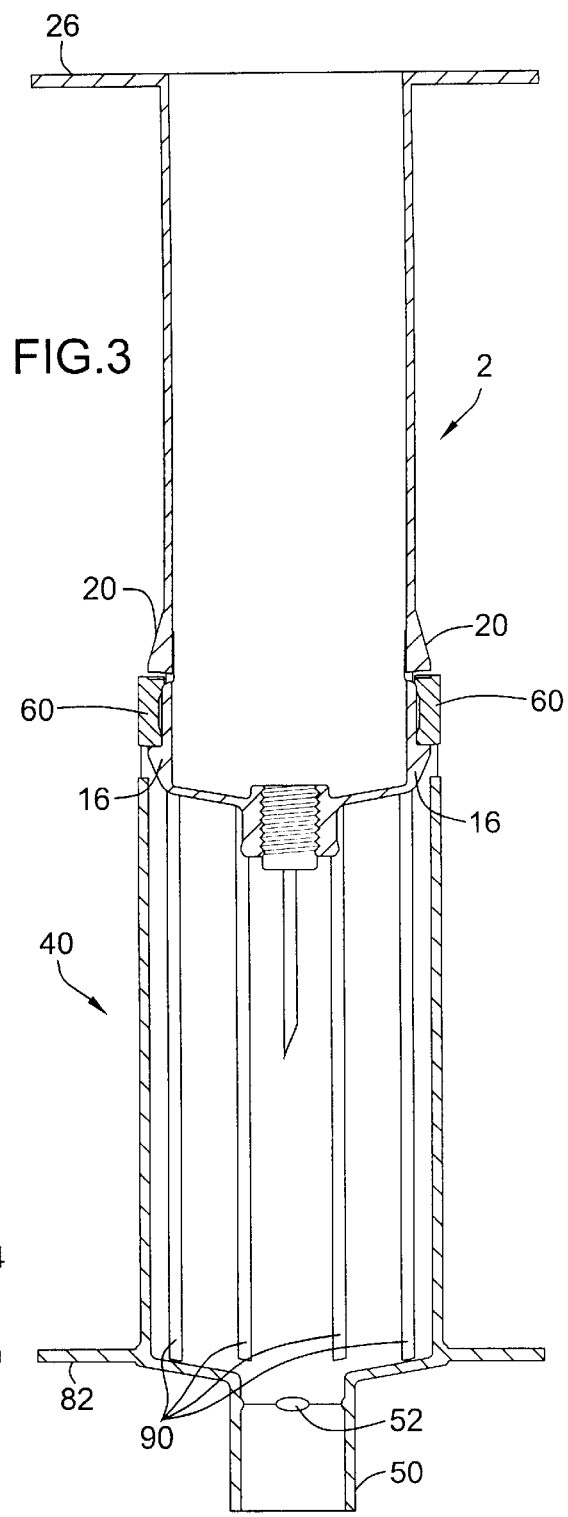
FIG. 3 is a view in longitudinal section of the fluid collection device of the invention with the receptacle in a locked position with respect to the shield and the needle retracted within the shield.

An exemplary embodiment of a fluid collection device having a shield of the present invention is illustrated in FIGS. 1–3. The fluid collection device includes a receptacle 2 and a shield 40. Both the receptacle and shield are typically cylindrical in shape and have open proximal ends and closed distal ends. However, it is noted that each member may have any geometric configuration that is consistent with operational features described herein. The receptacle and shield are each preferably single pieces and typically made from any conventional or other material utilized in making fluid collection devices; preferably, they are each molded as one piece from a clear, plastic material, such as polypropylene.

An internal cavity 6 is defined within receptacle 2 and extends axially between its closed distal end 8 and open proximal end 4. The receptacle internal cavity is typically dimensioned to receive a vial or other container for holding fluids extracted by a vacuum needle. A substantially cylindrical protruding tip 12 extends axially from receptacle distal end 8 and has a diameter that is smaller than the diameter of the receptacle. Protruding tip 12 is typically centered on the longitudinal axis of the receptacle; however, it may be positioned at any location along the receptacle distal end. The protruding tip is hollow and has an aperture 10 located at its end that is in communication with cavity 6 of the receptacle. Aperture 10 is typically dimensioned to receive and hold a needle assembly portion of a vacuum needle. The needle assembly may be affixed to the receptacle protruding tip by means of any conventional or other type fastener. Preferably, a vacuum needle 100 is attached to the receptacle protruding tip by means of a threaded fastener connection 102 as illustrated in FIGS. 2 and 3. Specifically, protruding tip 12 includes internal threads complimentary to external threads provided on the needle assembly of needle 100. A flange 26 extends radially from the exterior surface of receptacle 2 at its distal end 4 and provides a gripping surface for a user to engage the receptacle during axial movement of the receptacle with respect to the shield.

Shield 40 has an internal cavity 44 extending between its closed distal end 46 and its open proximal end 42. A cylindrical and hollow protruding tip 50 extends axially from shield distal end 46 and has a diameter that is typically smaller than the diameter of the shield. An aperture 48 is located at the end of the shield protruding tip and is in communication with shield cavity 44. The shield protruding tip is further dimensioned and aligned on the shield distal end 46 to telescopically receive protruding tip 12 of receptacle 2 and ensure alignment of the shield protruding tip aperture with the receptacle protruding tip aperture when the receptacle is nested within the shield. Aperture 48 of the shield is also appropriately dimensioned to allow a vacuum needle attached to the receptacle to alternatively extend from or retract within the shield. A flange 82 extends radially from the exterior surface of shield 40 at the shield distal end 46. The shield flange provides a gripping surface for a user to engage the shield during axial movement of the receptacle with respect to the shield.

The internal diameter of shield 40 is slightly larger than the external diameter of receptacle 2 to allow the receptacle to telescopically slide with relative ease within shield cavity 44. A plurality of ribs 90 radially protrude from the interior surface of shield 40 and typically extend in an axial direction along the shield interior surface for substantially the entire length of the shield cavity. However, it is noted that the ribs may extend in any fashion (e.g., circumferentially, in a spiral, etc.) within the shield. The ribs contact the exterior surface of receptacle 2 when the receptacle is inserted within the shield, thereby providing a sliding surface upon which the receptacle can be axially moved. The use of ribs within the shield and appropriate dimensioning of the shield inner diameter and receptacle outer diameter eliminates any frictional engagement between the shield interior surface and the receptacle exterior surface. Thus, a reduced surface area of frictional contact between the receptacle and shield is provided that facilitates easy sliding of one member with respect to the other while maintaining positional stability between the members.

A releasable locking feature for locking the receptacle with respect to the shield of the present invention in a "needle storage" mode is best illustrated in FIGS. 2 and 3. Receptacle 2 has a pair of engaging tabs 16 and a corresponding pair of locking tabs 20 positioned on the exterior surface of the receptacle near receptacle distal end 8. One engaging tab is axially aligned with one locking tab, and the two sets of engaging and locking tabs are typically symmetrically spaced along the circumference of the receptacle. Each engaging tab 16 is formed by a ramp having an inclined surface increasing in distance radially from the receptacle exterior surface and extending in an axial direction along the receptacle. The inclined surface of each engaging tab terminates in an engaging edge 24 facing the receptacle proximal end 4. Each locking tab 20 is positioned between an engaging tab 16 and receptacle proximal end 4 and is formed by a ramp having an inclined surface increasing in distance radially from the receptacle exterior surface and extending in an axial direction along the receptacle. The inclined surface of each locking tab terminates in a locking edge 28 facing the receptacle distal end 8. Each locking tab is further aligned with a corresponding engaging tab so that their locking and engaging edges face each other and are separated by a distance D.

A portion of the receptacle wall is removed in an area adjacent each locking tab 20, including an area surrounding locking edges 2. A longitudinal end of each locking tab 20 located opposite its locking edge 28 remains affixed to the receptacle so that the tabs are resiliently cantilevered in the resulting space or openings 32 formed by the removed portion of the receptacle wall. Locking tabs 20 are thereby free to be radially depressed towards the receptacle exterior surface and into their respective openings 32 upon application of a sufficient force to the inclined surface of the locking tabs. Upon removal of such applied force, the locking tabs resiliently spring back to their original position outside the profile of receptacle 2.

A pair of slots 54 is positioned on the interior surface of shield 40 proximate the shield proximal end 42. Each slot typically penetrates radially through the wall of the shield and is dimensioned to receive and engage a corresponding engaging tab 16 on the receptacle. Located adjacent the slots is a pair of protrusions 60. Each protrusion typically extends between a corresponding slot 54 and the open shield proximal end 42, with a distal edge 64 adjacent the corresponding slot and a proximal edge 62 adjacent the shield proximal end 42. The two sets of slots and protrusions are typically symmetrically spaced along the circumference of the shield. The length of each protrusion is less than or equal to the distance D between the engaging and locking tabs of the receptacle. Providing such a length allows engaging tabs 16 of the receptacle to be received within slots 54 when corresponding locking tabs 20 engage with the proximal edges 62 of protrusions 60. Upon engagement of the locking tabs with the protrusions, the proximal edge 62 of each protrusion essentially serves as a barrier to a corresponding locking tab 20 preventing the receptacle from moving axially toward the shield distal end 46 until the locking tabs are depressed. Similarly, each engaging tab abuts a distal edge 64 of a corresponding protrusion 60 to prevent the receptacle from moving axially toward the shield proximal end 42 when engaged in a corresponding slot. Preferably, the length of each protrusion is substantially equal to the distance D between the corresponding locking and engaging tabs so as to prevent any axial movement of the receptacle with respect to the shield when the engaging tabs and locking tabs are engaged with the slots and protrusions, respectively.

Each protrusion on the shield may further include a concave contour longitudinally aligned along its surface to facilitate a smooth transition for a corresponding locking tab moving between the edges of the protrusion into or out of a locking position. The contour of each protrusion 60 is typically formed by a first inclined section 70 extending from the protrusion distal edge 64 to a flat, intermediate section 72. The flat intermediate section 72 extends to a second inclined section 74 that ends at the protrusion proximal edge 62.

A pair of ribs 92 surrounds each set of slots and protrusions on the interior surface of the shield. The ribs 92 are sufficiently spaced to provide a channel for an engaging tab and locking tab to travel during axial displacement of the receptacle within the shield cavity. Preferably, the receptacle is prevented from any rotational movement with respect to the shield when its engaging and locking tabs are received and held within ribs 92.

An additional releasable locking feature for locking the device in a "needle exposure" mode is described below. Protruding tip 12 of receptacle 2 includes a flared ring portion 14 surrounding the exterior surface of the protruding tip at its end. The ring portion flares radially outward from the protruding tip in a direction away from the protruding tip end and toward the receptacle distal end 8. The shield protruding tip 50 includes a plurality of nibs 52 extending radially from its interior surface. The nibs are spaced circumferentially from each other and frictionally engage the ring portion 14 when the receptacle protruding tip is nested within the shield protruding tip and the needle is exposed for use. Preferably, the shield protruding tip includes four nibs spaced approximately 90° from each other along the circumference of its interior surface.

Axial movement of the receptacle within the shield between the two releasable locking positions is described below. During use of the device for collecting fluids, the receptacle is releasably locked with respect to the shield in a "needle exposure" position, wherein vacuum needle 100 extends from shield 40 (FIG. 2). The receptacle may be axially displaced within the shield cavity so that receptacle protruding tip 12 is fully nested within shield protruding tip 50 to allow needle 100 to fully extend through aperture 48 on the shield protruding tip. Ring portion 14 of the receptacle protruding tip frictionally engages nibs 52 on the interior surface of the shield protruding tip, resulting in a resistance to axial movement of the receptacle toward the shield proximal end 42. Such resistance can be easily overcome by an application of force, typically applied at receptacle flange 26, sufficient to allow ring portion 14 to travel over nibs 52 and axially displace the receptacle from shield cavity 44. The shield is also engaged, typically at shield flange 82, to prevent its movement during displacement of the receptacle within the shield.

During axial displacement of the receptacle from the shield cavity between the two locking positions, the exterior surface of the receptacle slides smoothly along ribs 90 within the shield, and the engaging tabs 16 and locking tabs 20 travel within the channels formed by ribs 92. Upon contact with the first inclined section 70 of a respective protrusion 60, a corresponding locking tab 20 is pressed radially inward into its opening 32 until it clears the edge of the first inclined section. After clearing the edge of the first inclined section, the locking tab resiliently springs outward to a point where its ramp contacts the concave contour of the protrusion. The locking tab slides along the concave contour as the receptacle continues to be axially displaced from the shield cavity. Upon reaching the transition between a corresponding middle section 72 and second inclined section 74, locking tab 20 is pressed once again into opening 32 until the locking tab edge 28 reaches a corresponding proximal edge 62 of the protrusion. At such position the locking tab springs radially outward so that its locking edge 28 abuts protrusion proximal edge 62. The protrusion proximal edges 62 serve as barriers to locking tabs 20 to prevent the receptacle from moving axially toward the shield distal end 46. Each engaging tab 16 is received in a respective slot 54 with engaging tab edges 24 abutting protrusion distal edges 64 upon abutment of the locking tab edges with the protrusion proximal edges. Thus, the receptacle is effectively prevented from axial displacement toward either end of the shield and the device is in a locked "needle storage" position as illustrated in FIG. 3 (i.e., needle 100 is completely retracted within shield 40).

The device may further be released from the locked "needle storage" position by applying sufficient force to depress locking tabs 20 into openings 32. Such depression of the locking tabs disengages their edges 28 from the protrusion proximal edges 62 to allow for axial displacement of the receptacle within the shield cavity. The releasable locking features and the ease with which needles may be replaced on the receptacle allow the device to be used for multiple fluid collection operations where an attached needle may be shielded an unlimited number of times.

It will be appreciated that the fluid collection device with protective shield of the present invention may be implemented in many ways in addition to the exemplary embodiment described above and illustrated in the drawings.

The shield and receptacle may have any geometric configuration and may be constructed of any material suitable for facilitating operation of the device. Each member may include one or more flanges along their exterior surfaces for providing a gripping surface for a user. The location of flanges for the shield may be anywhere along its exterior surface. The protruding tips may be aligned anywhere along the distal ends of the receptacle and shield. Alternatively, the protruding tip on each member may be replaced with an aperture on its distal end to facilitate the attachment of a vacuum needle directly to the receptacle distal end as well as provide an opening for passage of the needle directly at the shield distal end. The nibs on the shield protruding tip may be of any number and have any geometrical configuration. Alternatively, the nibs may be replaced with any radially protruding member disposed around at least a portion of the circumference of the interior surface of the protruding tip. The ribs on the interior surface of the shield may be of any number and may extend in any direction or manner (e.g., spiral, linear, circumferential, etc.) along the shield interior surface.

The placement of engaging tabs and locking tabs as well as slots and protrusions can be anywhere along the surface of the receptacle or shield, so long as sufficient distance is provided in the shield cavity for completely receiving a vacuum needle when the device is locked in the "needle storage" position. It is preferable to place the engaging and locking tabs near the receptacle distal end and the slots and protrusions near the shield proximal end, as set forth in the embodiment of FIGS. 1–3, so as to maximize the distance within the shield cavity that the needle may be retracted in the "needle storage" position. Any number of engaging tabs and locking tabs (e.g., one engaging tab and one locking tab) may be employed on the receptacle. Similarly, any number of slots and protrusions (e.g., one slot and one protrusion) may be employed on the shield. The shield protrusions may further be eliminated when the shield slots are located near the shield proximal end such that the proximal edge of the shield serves as a barrier for the receptacle locking tabs. The locking tabs may be aligned in an axial direction of the receptacle or in any other manner with the engaging tabs along the receptacle exterior surface. Similarly, the protrusions may be aligned in an axial direction of the shield or in any other manner with the slots along the shield interior surface. Pairs of tabs and corresponding protrusions and slots may also be aligned in any manner (e.g., symmetrically) along the receptacle and shield.

From the foregoing description, it will be appreciated that the invention makes available a novel fluid collection device with protective shield employing releasable locking features in both a "needle exposure" position and a "needle storage" position.

Having described preferred embodiments of a new and improved fluid collection device with protective shield, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A fluid collection device comprising:

a receptacle having a closed distal end, an open proximal end and an internal cavity defined therebetween, wherein said receptacle distal end includes an aperture in communication with said receptacle internal cavity and is configured to receive and retain a vacuum needle;

said receptacle including at least one engaging tab and at least one locking tab protruding from an exterior surface of said receptacle at axially spaced locations, wherein said engaging tab includes an inclined surface increasing in radial distance from an exterior surface of said receptacle and extending in an axial direction to terminate at an engaging edge facing said receptacle proximal end, and said locking tab is located between said engaging tab and said receptacle proximal end and includes an inclined surface increasing in radial distance from said receptacle exterior surface and extending in an axial direction to terminate at a locking edge facing said receptacle distal end; and a shield having a closed distal end, an open proximal end and an internal cavity defined therebetween, wherein said shield internal cavity is dimensioned to telescopically receive at least a portion of said receptacle and said shield distal end includes an aperture in communication with said shield internal cavity and aligned with said receptacle aperture to allow passage of said vacuum needle retained by said receptacle into and out of said shield internal cavity;

said shield including at least one slot and at least one barrier defined along an interior surface of said shield, wherein said slot is configured to fully receive and hold said engaging tab when said receptacle is axially displaced within said shield cavity toward said shield proximal end, and said barrier is located between said slot and said shield proximal end and configured to engage said locking edge of said locking tab when said engaging tab is fully received and held in said slot.

2. The fluid collection device of claim 1, wherein said barrier engages said locking edge of said locking tab at said shield proximal end.

3. The fluid collection device of claim 1, wherein said locking tab is deformable in a radial direction toward said receptacle to disengage said locking edge of said locking tab from said barrier upon application of a sufficient force to said locking tab.

4. The fluid collection device of claim 3, wherein said locking tab is resiliently cantilevered on said receptacle exterior surface.

5. The fluid collection device of claim 1, wherein said shield has a plurality of ribs disposed along said shield interior surface to frictionally engage said receptacle as said receptacle is axially displaced within said shield cavity.

6. The fluid collection device of claim 5, wherein said engaging tab and said locking tab are aligned in an axial direction along said receptacle exterior surface, and said slot and said barrier are aligned in an axial direction along said shield interior surface.

7. The fluid collection device of claim 6, wherein said slot and said barrier are bordered by a pair of substantially parallel and circumferentially spaced ribs extending in an axial direction along said shield interior surface, and said pair of substantially parallel and circumferentially spaced ribs define a guide channel therebetween to receive said engaging tab and said locking tab.

8. The fluid collection device of claim 1, wherein said barrier includes a distal end adjacent said slot and a proximal end adjacent said shield proximal end, and, upon receipt of said engaging tab in said slot and engagement of said locking tab with said barrier, said barrier distal end abuts said engaging edge of said engaging tab and said barrier proximal end abuts said locking edge of said locking tab.

9. The fluid collection device of claim 1, wherein said receptacle includes a radially extending flange near said receptacle proximal end and said shield includes a radially extending flange near said shield distal end.

10. The fluid collection device of claim 1, wherein said receptacle distal end includes a hollow protruding tip extending axially between said receptacle cavity and said receptacle aperture, and said shield distal end includes a hollow protruding tip extending axially between said shield cavity and said shield aperture, and said shield protruding tip is aligned on said shield to telescopically receive said receptacle protruding tip when said receptacle distal end is adjacent said shield distal end.

11. The fluid collection device of claim 10, wherein a ring portion surrounds an exterior surface of said receptacle protruding tip, said ring portion being radially flared in a direction facing said receptacle cavity, and at least one nib extends from an interior surface of said shield protruding tip to frictionally engage said ring portion when said receptacle protruding tip is telescopically received within said shield protruding tip.

12. An improved fluid collection device having a shield and a receptacle telescopically received therein, said receptacle configured for axial displacement within said shield, the improvement comprising:

a first locking means for releasably locking said receptacle within said shield at a selected distance between a distal end of said receptacle and a distal end of said shield; and a second locking means for releasably locking said receptacle within said shield when said receptacle distal end is substantially adjacent said shield distal end, wherein said second locking means is defined at said receptacle and shield distal ends.

13. The improved fluid collection device of claim 12, wherein said first locking means includes:

a receptacle engaging means disposed on an exterior surface of said receptacle, said receptacle engaging means for releasably engaging said shield and preventing said receptacle from being axially displaced toward a proximal end of said shield;

a receptacle locking means disposed on an exterior surface of said receptacle, said receptacle locking means for releasably engaging said shield and preventing said receptacle from being axially displaced toward said shield distal end;

a shield receiving means defined on an interior surface of said shield, said shield receiving means for completely receiving and holding said receptacle engaging means when said receptacle distal end is displaced the selected distance from said shield distal end; and a shield locking means defined at an interior surface of said shield, said shield locking means for engaging said receptacle locking means and preventing said receptacle from being axially displaced toward said shield distal end when said receptacle engaging means is received and held in said shield receiving means.

14. The improved fluid collection device of claim 13, wherein said shield locking means engages said receptacle locking means at said shield proximal end.

15. The improved fluid collection device of claim 13, wherein said receptacle locking means is deformable in a radial direction toward said receptacle to disengage said receptacle locking means from said shield locking means upon application of a sufficient force upon said receptacle locking means.

16. A method of releasably locking a receptacle within a cavity of a shield of a fluid collection device to prevent axial displacement of said receptacle with respect to said shield, wherein said receptacle is telescopically received within said shield cavity and includes at least one engaging tab and at least one locking tab spaced in an axial direction on an exterior surface of said receptacle, said shield includes at least one slot and at least one barrier disposed on an interior surface of said shield, and said receptacle and said shield each include a corresponding locking mechanism disposed proximate their closed distal ends, the method comprising:

(a) axially displacing said receptacle within said shield cavity until said locking tab engages said barrier and said engaging tab is fully received and held within said slot to thereby prevent further axial displacement of said receptacle within said shield cavity;

(b) applying a force to said locking tab to radially deform said locking tab in a direction toward said receptacle and disengage said locking tab and said barrier;

(c) axially displacing said receptacle within said shield cavity to remove said engaging tab from said slot; and (d) axially displacing said receptacle within said shield cavity in a direction toward said shield closed distal end until said locking mechanism disposed proximate said receptacle closed distal end engages said locking mechanism disposed proximate said shield closed distal end to thereby lock said receptacle with respect to said shield.

* * * * *